(12) United States Patent
Agarwal et al.

(10) Patent No.: US 8,980,881 B2
(45) Date of Patent: *Mar. 17, 2015

(54) CRYSTALLINE FORMS OF (R)-8-CHLORO-1-METHYL-2,3,4,5-TETRAHYDRO-1H-3-BENZAZEPINE HYDROCHLORIDE

(75) Inventors: Rajesh K. Agarwal, San Diego, CA (US); William L. Betts, III, San Diego, CA (US); James A. Henshilwood, Carlsbad, CA (US); Yuan-Hon Kiang, Newbury Park, CA (US); Noah Post, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 13/616,887

(22) Filed: Sep. 14, 2012

(65) Prior Publication Data

US 2014/0051684 A1 Feb. 20, 2014

Related U.S. Application Data

(63) Continuation of application No. 13/425,669, filed on Mar. 21, 2012, now Pat. No. 8,697,686, which is a continuation of application No. 11/793,473, filed as application No. PCT/US2005/046983 on Dec. 20, 2005, now Pat. No. 8,168,624.

(60) Provisional application No. 60/638,221, filed on Dec. 21, 2004.

(51) Int. Cl.
| | | |
|---|---|---|
| A61K 31/55 | (2006.01) | |
| C07D 223/16 | (2006.01) | |
| A61P 3/04 | (2006.01) | |

(52) U.S. Cl.
CPC .................................. *C07D 223/16* (2013.01)
USPC ..................................... 514/217.01; 540/594

(58) Field of Classification Search
CPC .............................. A61K 31/55; C07D 223/16
USPC ........................................ 514/217.01; 540/594
See application file for complete search history.

(56) References Cited

U.S. PATENT DOCUMENTS

| | | | |
|---|---|---|---|
| 3,652,543 A | 3/1972 | Hoegerle | |
| 3,716,639 A | 2/1973 | Hoegerle et al. | |
| 3,795,683 A | 3/1974 | Brossi et al. | |
| 4,108,989 A | 8/1978 | Holden | |
| 4,111,957 A | 9/1978 | Holden et al. | |
| 4,210,729 A | 7/1980 | Hermans et al. | |
| 4,210,749 A | 7/1980 | Shetty | |
| 4,233,217 A | 11/1980 | Shetty | |
| 4,762,845 A | 8/1988 | Chu et al. | |
| 4,988,690 A | 1/1991 | Effland et al. | |
| 5,015,639 A | 5/1991 | Berger et al. | |
| 5,178,786 A | 1/1993 | Jahnke et al. | |
| 5,275,915 A | 1/1994 | Kojima et al. | |
| 5,387,685 A | 2/1995 | Powell et al. | |
| 5,412,119 A | 5/1995 | Brussee et al. | |
| 5,422,355 A | 6/1995 | White et al. | |
| 5,691,362 A | 11/1997 | McCormick et al. | |
| 5,750,520 A | 5/1998 | Danilewicz et al. | |
| 5,856,503 A | 1/1999 | Aebi et al. | |
| 5,861,393 A | 1/1999 | Danilewicz et al. | |
| 5,925,651 A | 7/1999 | Hutchinson | |
| 5,939,415 A | 8/1999 | Laufer et al. | |
| 5,942,535 A | 8/1999 | Laufer et al. | |
| 5,958,943 A | 9/1999 | Laufer et al. | |
| 6,087,346 A | 7/2000 | Glennon et al. | |
| 6,218,385 B1 | 4/2001 | Adam et al. | |
| 6,900,313 B2 | 5/2005 | Wasserscheid et al. | |
| 6,953,787 B2 | 10/2005 | Smith et al. | |
| 6,972,295 B2 | 12/2005 | Hagmann et al. | |
| 7,514,422 B2 | 4/2009 | Smith et al. | |
| 7,977,329 B2 | 7/2011 | Smith et al. | |

FOREIGN PATENT DOCUMENTS

| | | |
|---|---|---|
| CA | 1090797 | 12/1980 |
| CA | 2197789 | 8/1995 |
| CH | 500194 | 1/1971 |
| DE | 1944121 | 3/1970 |
| DE | 3315106 A1 | 11/1983 |
| EP | 0007070 | 1/1980 |
| EP | 0080779 A1 | 6/1983 |
| EP | 0096838 | 12/1983 |
| EP | 0161350 A1 | 11/1985 |
| EP | 0174118 | 3/1986 |
| EP | 0285287 A3 | 3/1987 |
| EP | 0285919 B1 | 10/1988 |
| EP | 0987235 A1 | 3/2000 |
| EP | 1074549 A2 | 2/2001 |
| EP | 0987235 B1 | 3/2003 |
| GB | 1221324 | 2/1971 |
| GB | 1225053 | 3/1971 |

(Continued)

OTHER PUBLICATIONS

Barnes, "Pharmacological Strategies for Relapse Prevention in Schizophrenia," Psychiatry 3(10): 37-40 (2004).
Bickerdike, "5-HT$_{2C}$ Receptor Agonists as Potential Drugs for the Treatment of Obesity," Current Topics in Medicinal Chemistry, vol. 3:pp. 885-897 (2003).
Chahal et al., IDdb Meeting Report 2000, May 17-18.
Chang et al., "Dopamine Receptor Binding Properties of Some 2,3,4,5-tetrahydro-1H-3-benzazepine-7-OLS with Non-Aromatic Substituents in the 5-Position," Bioorganic & Medicinal Chemistry Letters, 2(5):399-402 (1992).
Deady et al., "Synthesis of Some Tetrahydro-2- and 3-benzazepines, and of Hexahydro-3-benzazocine," JCS Perkin I, 782-3 (1973).
Di Chiara et al., "Nucleus accumbens shell and core dopamine: differential role in behavior and addiction," Behavioural Brain Research, 137: 75-114 (2002).
Di Chiara et al., "Reward System and Addiction: What Dopamine Does and Doesn't Do," Current Opinion in Pharmacology 7:69-76 (2007).

(Continued)

*Primary Examiner* — Sreeni Padmanabhan
*Assistant Examiner* — Sahar Javanmard

(57) ABSTRACT

The present invention is directed to crystalline forms of (R)-8-chloro-1-methyl-2,3,4,5-tetrahydro-1H-3-benzazepine, compositions containing the same and uses thereof.

4 Claims, 12 Drawing Sheets

(56) References Cited

FOREIGN PATENT DOCUMENTS

| | | |
|---|---|---|
| GB | 1268243 | 3/1972 |
| GB | 1599705 | 10/1981 |
| JP | 5339263 | 12/1993 |
| JP | 06298746 | 10/1994 |
| JP | 08134048 | 5/1996 |
| JP | 09030960 | 2/1997 |
| JP | 90987258 | 3/1997 |
| NL | 7807819 | 7/1978 |
| WO | WO 88/07858 | 10/1988 |
| WO | WO 91/19698 | 12/1991 |
| WO | WO 93/00094 | 1/1993 |
| WO | WO 95/13274 | 5/1995 |
| WO | WO 96/04271 | 2/1996 |
| WO | WO 96/05194 A1 | 2/1996 |
| WO | WO 96/33993 A1 | 10/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02/074746 | 9/2002 |
| WO | WO 03/000663 A1 | 1/2003 |
| WO | WO 03/027068 A2 | 4/2003 |
| WO | WO 03/062392 A2 | 7/2003 |
| WO | WO 03/086306 A2 | 10/2003 |
| WO | WO 2004/037788 | 5/2004 |
| WO | WO 2005/003096 A1 | 1/2005 |
| WO | WO 2005/019179 A2 | 3/2005 |
| WO | WO 2005/042490 A1 | 5/2005 |
| WO | WO 2005/042491 A1 | 5/2005 |
| WO | WO 2006/013209 A2 | 2/2006 |
| WO | WO 2006/043710 | 4/2006 |
| WO | WO 2006/069363 A2 | 6/2006 |
| WO | WO 2006/071740 A2 | 7/2006 |
| WO | WO 2007/120517 A2 | 10/2007 |

OTHER PUBLICATIONS

Di Giovanni et al., "Serotonin/dopamine interaction—Focus on 5-HT$_{2C}$ receptor, a new target of psychotropic drugs," Indian Journal of Experimental Biology, vol. 40:pp. 1344-1352 (2002).

Di Matteo et al. et al., "Role of 5-HT$_{2C}$ Receptors in the Control of Central Dopamine Function," *Trends in Pharmacological Sciences* 22(5):229-232 (2001).

Diagnostic and Statistical Manual of Mental Disorders, 4th edition, Text Revision, Washington, DC, American Psychiatric Association, 2000*.

Flannery-Schroeder, "Reducing Anxiety to Prevent Depression," *Am. J. Prev. Med.* 31 (6S1):S136-S142 (2006).

Fuchs et al., "Total synthesis of (+/−)-lennoxamine and (+/−)-aphanorphine by intramolecular electrophilic aromatic substitution reactions of 2-amidoacroleins," Organic Letters, 2001, pp. 3923-3925, 3(24).

Gallant et al., "U-22,394A: a controlled evaluation in chronic schizophrenic patients," Current Therapy Research 9(11):579-81(1967).

Gardent et al., "Sur Quelques Propriétés de l'Amino-2 Bromo-4 1H Benzazépine-3 et de ses dérivés," Bulletin de La Société Chimique de France, 2:600-5 (1968) French Lang Only.

Gerace et al., "Predictors of Weight Increases over 7 Years in Fire Fighters and Paramedics," Preventive Medicine 25:593-600 (1996).

Gobert et al., "Serotonin$_{2C}$ Receptors Tonically Suppress the Activity of Mesocortical Dopaminergic and Adrenergic, But Not Serotonergic, Pathways: A Combined Dialysis and Electrophysiological Analysis in the Rat," Synapse 36: 205-221 (2000).

Gombar et al., "Pharmacokinetics of a series of 6-chloro-2, 3, 4, 5-tetrahydro-3-substituted-1H-3-benzazepines in rats," Drug Metab. Disposition 16:367-372 (1988).

Greene et al., Protective Groups in Organic Syntheses, 2nd Ed., Wiley and Sons, NY (1991)**ref excessively voluminous; provided upon request.

Greisser "Polymorphism in the Pharmaceutical Industry," ed. Rolf Hilfier, Wiley-VCH Verlag GmbH & Co.: pp. 211-233 (2006).

Guillory, "Polymorphism in Pharmaceutical Solids," ed. Harry G. Brittain, Marcel Dekker, Inc., vol. 95: pp. 202-209 (1999).

Halford, "Serotonergic Drugs: Effects on Appetite Expression and Use for the Treatment of Obesity," *Drugs* 67(1):27-55 (2007).

Halford, J.C.G., "Obesity Drugs in Clinical Development," *Current Opinion in Investigational Drugs* 7(4):312-318 (2006).

Hassine-Coniac, et al., et al., "Preparation et propriétés d'aldéhydes dans la série de la benzazépine-3," Bulletin de La Société Chimique de France, 11:3985-92 (1971) French Lang Only.

Hazebroucq, "Accès A Des $_1$-H, Tètrahydro-2, 3, 4,5 Benzazèpines-$_3$ One-$_1$, et a Des Hexahydro Imidazo Isoquinoléines," Ann. Chim., t.1:221-54 (1966) French Lang Only.

Hester et al., "Azepinoindoles. I. Hexahyclroazepino[4,5-b]indoles," J. Med. Chem. 11(1): 101-106 (1968).

Higgins et al. "Serotonin and drug reward: focus on 5-HT$_{2C}$ receptors," European Journal of Pharmacology, 480: 151-162 (2003).

Hitzig, P., "Combined serotonin and dopamine indirect agonists correct alcohol craving and alcohol-associated neuroses," Journal of Substance Abuse Treatment, 11(5):489-90 (1994).

Im et al., "Positive Allosteric Modulator of the Human 5-HT$_{2C}$ Receptor," Molecular Pharmacology, 64: 78-84 (2003).

Jandacek, R.J., "APD-356 (Arena)," *Current Opinion in Investigational Drugs* (6(10):1051-1056 (2005).

Jenck, et al., "Antiaversive effects of 5HT$_{2C}$ receptor agonists and fluoxetine in a model of panic-like anxiety in rats," European Neuropsychopharmacology 8: 161 (1998).

Jensen et al., "Potential Role of New Therapies in Modifying Cardiovascular Risk in Overweight Patients with Metabolic Risk Facts," *Obesity* 14 (Suppl. 3):143S-149S (2006).

Karasu et al., (2000) Practice Guideline for the Treatment of Patients with Major Depressive Disorder.

Koplan et al., "Preventing Childhood Obesity: Health in the Balance, Executive summary," (2005).

Lacivita et al., "Selective Agents for Serotonin$_{2C}$ (5-HTC$_{2C}$) Receptor," Current Topics in Medicinal Chemistry, vol. 6:pp. 1927-1970 (2006).

Ladd et al., "Synthesis of a Dopaminergic Binding of 2-Aryldopamine Analogues: Phenethylamines, 3-Benzazepines, and 9-(Aminomethyl) Fluorenes," B209 J. Med. Chem., 29(10):1904-12 (1986).

Lam et al., Canadian Consensus Guidelines for the Treatment of Seasonal Affective Disorder, Clinical & Academic Publishing, Vancouver, BC, Canada.

Lennon et al, "Azabenzocycloheptenones. Part XVIII.[1] Amines and Amino-ketones of the Tetrahydro-3-benzazepin-1-one Series," J.C. S. Perkin I,7:622-6 (1975).

MacDonald et al., "Design and Synthesis of *trans*-3-(2-(4-((3-(3-(5-methyl-1,2,4-oxadiazolyl))-phenyl)carboxamido)cyclohexyl)ethyl)-7-methylsulfonyl-2,3,4,5-tetrahydro-1*H*-3-benzazepine (SB-414796): A Potent and Selective Dopamine D$_3$ Receptor Antagonist," J. Med. Chem., 46(23):4952-64 (2003).

Moline et al., "Postpartum Depression: A Guide for Patients and Families," Expert Consensus Guidelines Series—Treatment of Depression in Woman Mar. 2001: 112-113 (2001).

Muller et al., "Intracellular 5-HT$_{2C}$-receptor dephosphorylation: a new target for treating drug addiction," Trends in Pharmacological Sciences, 27(9):455-58 (2006).

Nagase et al., "An anhydrous polymorphic form of trehalose," *Carbohydrate Research* 337(2),167-173 (2002).

Navarro-Vazquez et al., "A study of aryl radical cyclization in enaminone esters," J. Org. Chem. 67:3213-20 (2002).

Niendam et al., "Neurocognitive Performance and Functional Disability in the Psychosis Prodrome," Schizophrenia Research 84:100-111 (2006).

Orito et al., "Total synthesis of pseudo type of protopine alkaloids," Heterocycles 14(1), 11-14 (1980).

Orito et al., Hokkaido Daigaku Kogakubu Kenkyu Hokoku (1979), (96), 41-44.

Pauvert et al., "Silver Nitrate-Promoted Ring Enlargement of 1-tribromomethyl-1,2-dihydro- and 1-tribromethyl-1,2, 3,4-

(56) References Cited

OTHER PUBLICATIONS tetrahydro-isoquinoline Derivatives: Application to the Synthesis of the Anti-anginal Zatebradine," Tetrahedron Letters, 44:4203-6 (2003), Pergamon Press Ltd.

Pawan et al., "Preliminary study on the effects of fenfluramine derivative, 'S992' in man," British Journal of Pharmacology, 41(2): 416P-417P (1971).

Pecherer et al., "The Synthesis of Some 7- and 7,8-substituted 2,3,4,5-tetrahydro-1H-3-benzazepines," J. Heterocyclic Chemistry 8(5):779-783 (1971).

Perry et al., "Prospective study of risk factors for development on non-insulin dependent diabetes in middle aged British men," BMJ (1995) 310:560-564.

Piesla et al., (2001) Schizophrenia Research 49: 95.

Porras, et al., "5-$HT_{2A}$ and 5-$HT_{2C/2B}$ Receptor Subtypes Modulate Dopamine Release Induced in Vivo by Amphetamine and Morphine in Both the Rat Nucleus Accumbens and Striatum," Neuropsychopharmacology 26: 311-324 (2002).

Prous Science Integrity entry 156186.

Prous Science Integrity entry 354056.

Rothman, R.B., "Treatment of Alcohol and Cocaine Addiction by the Combination of Pemoline and Fenfluramine: A Preliminary Case Series," Journal of Substance Abust Treatment, 12(6):449-53 (1995).

Schaffner et al., "Preventing Severe Mental Illnesses—New Prospects and Ethical Challenges," *Schizophrenia Research* 51:3-15 (2001).

Schlademan et al., "Synthesis of oxo- and 1-hydroxy-azobenzocycloalkanes," J. Chem. Soc. Perkin Transacts. (1972) 2:213-215.

Smith et al, "Discovery and Structure-Activity Relationship of (1R)-8-Chloro-2,3,4,5-tetrahydro-1-methyl-1H-3-benzazepine (Lorcaserin), a Selective Serotonin 5-HT2c Receptor Agonist for the Treatment of Obesity," J. Med. Chem. 2008, 51, 305-313.

Smith et al., "Discovery and SAR of new benzazepines as potent and selective 5HT2C receptor agonists for the treatment of obesity." Bior. Med. Chem Leet. 15(5):1467-1470 (2005).

Tietze et al., "Efficient synthesis of 2, 3, 4, 5-tetrahydro-1H-3-benzazepines by intramolecular Heck reaction," Papers, Synthesis 876:880 (Sep. 1993).

Tsuang et al., "Towards the Prevention of Schizophrenia," B245 Biol. Psychiatry 48:349-356 (2000).

Van Oekelen et al., "5-$HT_{2A}$ and 5-$HT_{2C}$ receptors and their atypical regulation properties," Life Sciences, vol. 72:pp. 2429-2449 (2003).

Vink et al., "Risk Factors for Anxiety and Depression in the Elderly: A Review," J. Affect. Disord., vol. 106, p. 29-44 (2008).

Williams, Chemistry Demystified 123 (2003).

Wise, "Addiction Becomes a Brain Disease," Neuron, 26: 27-33 (2000).

Wisner et al., "Postpartum Depression," N. Engl. J. Med., 347(3):194-199 (2002).

Woods et al., "Annual Report: Evaluation of New Compounds for Opoid Activity," National Institute on Drug Abuse, Proceedings of the 41st Annual Scientific Meeting (1979) pp. 356-401.

Yoshinaga et al., "Prevention of Mildly Overweight Children from Development of More Overweight Condition," *Prevention Medicine* 38:172-174 (2004).

TGA Form II

CRYSTALLINE FORMS OF (R)-8-CHLORO-1-METHYL-2,3,4,5-TETRAHYDRO-1H-3-BENZAZEPINE HYDROCHLORIDE

CROSS-REFERENCE TO RELATED APPLICATIONS

This application is a continuation of U.S. patent application Ser. No. 13/425,669, filed Mar. 21, 2012, now U.S. Pat. No. 8,697,686 which is a continuation of U.S. patent application Ser. No. 11/793,473, filed Nov. 2, 2007, now issued as U.S. Pat. No. 8,168,624, which is a National Stage Entry of International Patent Application No. PCT/US05/46983, filed Dec. 20, 2005, and claims the benefit of U.S. Provisional Patent Application No. 60/638,221 filed Dec. 21, 2004; each of which is hereby incorporated by reference for all purposes.

FIELD OF THE INVENTION

The present invention relates to crystalline forms of the 5-$HT_{2C}$ agonist, (R)-8-chloro-1-methyl-2,3,4,5-tetrahydro-1H-3-benzazepine hydrochloride, compositions thereof and methods of using the same.

BACKGROUND OF THE INVENTION

Serotonin (5-HT) neurotransmission plays an important role in numerous physiological processes both in health and in psychiatric disorders. As an example, 5-HT has been implicated in the regulation of feeding behavior. It is believed that 5-HT induces a feeling of fullness or satiety so that eating stops earlier and fewer calories are consumed. As the 5-$HT_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, development of a selective 5-$HT_{2C}$ receptor agonist is desirable, having improved efficacy and safety over other anti-obesity agents and related drugs.

The compound, (R)-8-chloro-1-methyl-2,3,4,5-tetrahydro-1H-3-benzazepine, whose structure is shown below in Formula I, belongs to a class of 5-$HT_{2C}$ agonists that are useful in the treatment of a number of 5-$HT_{2C}$-related diseases and disorders, such as those mentioned above. Preparation and characterization of this compound are described in WO 2003/086306, which is incorporated herein by reference in its entirety. Preparation and characterization of the hydrochloric acid salt of this compound is also described in International Application No. PCT/US04/19279 which is incorporated herein by reference in its entirety. Because drug compounds having, for example, improved stability, solubility, shelf life, and in vivo pharmacology, are consistently sought, there is an ongoing need for new or purer salts, hydrates, solvates, and polymorphic crystalline forms of existing drug molecules. The crystalline forms of (R)-8-chloro-1-methyl-2,3,4,5-tetrahydro-1H-3-benzazepine hydrochloride described herein help meet this and other needs.

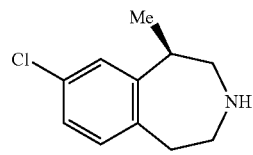

(R)-8-Chloro-1-methyl-2,3,4,5-tetrahydro-1H-3-benzazepine

SUMMARY OF THE INVENTION

Figure 1:
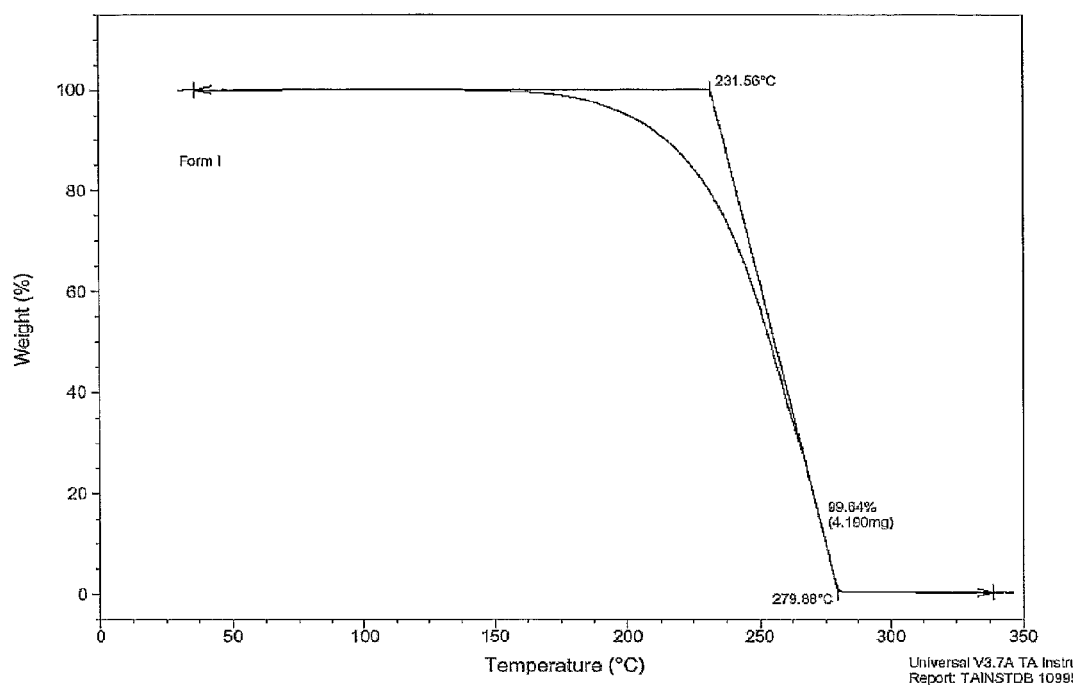
FIG. 1 depicts a thermogravimetric analysis (TGA) thermogram for crystalline Form I of the invention (TA Instruments TGA Q500 in open cell; 25-350° C.; 10° C./min).

In some embodiments, the present invention provides (R)-8-chloro-1-methyl-2,3,4,5-tetrahydro-1H-3-benzazepine hydrochloride hemihydrate.

In some embodiments, the present invention provides (R)-8-chloro-1-methyl-2,3,4,5-tetrahydro-1H-3-benzazepine hydrochloride hemihydrate having crystal Form III.

In some embodiments, the present invention provides (R)-8-chloro-1-methyl-2,3,4,5-tetrahydro-1H-3-benzazepine hydrochloride Form I.

In some embodiments, the present invention provides (R)-8-chloro-1-methyl-2,3,4,5-tetrahydro-1H-3-benzazepine hydrochloride Form II.

In some embodiments, the present invention provides compositions comprising the crystalline forms of the invention.

In some embodiments, the present invention provides processes for preparing the crystalline forms of the invention as well as crystalline forms prepared by the processes.

In some embodiments, the present invention provides methods for modulating a $5HT_{2C}$ receptor comprising contacting said receptor with a crystalline form herein.

In some embodiments, the present invention provides methods of treating disorders of the central nervous system; damage to the central nervous system; cardiovascular disorders; gastrointestinal disorders; diabetes insipidus, or sleep apnea by administering to a patient in need a therapeutically effective amount of a hemihydrate or crystal form described herein.

In some embodiments, the present invention provides methods of decreasing food intake of a mammal comprising administering to said mammal a therapeutically effective amount of a hemihydrate or crystal form described herein.

In some embodiments, the present invention provides methods of inducing satiety in a mammal comprising administering to said mammal a therapeutically effective amount of a hemihydrate or crystal form as described herein.

In some embodiments, the present invention provides methods of controlling weight gain of a mammal comprising administering to said mammal a therapeutically effective amount of a hemihydrate or crystal form as described herein.

In some embodiments, the present invention provides methods of treating obesity comprising administering to a patient a therapeutically effective amount of a hemihydrate or crystal form as described herein.

In some embodiments, the present invention provides use of a compound or crystal form of the invention for use in therapy.

In some embodiments, the present invention provides use of a compound or crystal form of the invention for use in the preparation of a medicament for use in therapy.

DETAILED DESCRIPTION

Crystalline Forms

The present invention provides, inter alia, three crystalline forms of (R)-8-chloro-1-methyl-2,3,4,5-tetrahydro-1H-3-benzazepine hydrochloride, individually designated as Form I, Form II, and Form III. Forms I and II are anhydrous, hygroscopic forms, both of which readily convert to Form III, a hemihydrate, upon exposure to moisture.

The various crystalline forms of (R)-8-chloro-1-methyl-2,3,4,5-tetrahydro-1H-3-benzazepine hydrochloride can be identified by their unique solid state signatures with respect to, for example, differential scanning calorimetry (DSC), X-ray powder diffraction (XRPD), and other solid state methods. Further characterization with respect to water or solvent content of the crystalline forms can be gauged by any of various routine methods such as thermogravimetric analysis (TGA), dynamic vapor sorption (DVS), DSC and other techniques. For DSC, it is known that the temperatures observed will depend upon the rate of temperature change as well as sample preparation technique and the particular instrument employed. Thus, the values reported herein relating to DSC thermograms can vary by plus or minus about 4° C. For XRPD, the relative intensities of the peaks can vary, depending upon the sample preparation technique, the sample mounting procedure and the particular instrument employed. Moreover, instrument variation and other factors can often affect the 2-theta values. Therefore, the peak assignments of diffraction patterns can vary by plus or minus about 0.2°. The physical properties distinguishing each of the three crystalline forms of the invention are summarized in Table I below.

TABLE 1

|  | Form I | Form II | Form III |
|---|---|---|---|
| TGA | FIG. 1;<br>negligible weight loss below 150° C. | FIG. 5;<br>negligible weight loss below 150° C. | FIG. 9;<br>3.7% water loss |
| DSC | FIG. 2;<br>201° C. (melt) | FIG. 6;<br>201° C. (melt) | FIG. 10;<br>95° C. (dehydration);<br>200° C. (melt) |
| XRPD | FIG. 3; | FIG. 7;<br>11.4° unique | FIG. 11;<br>13.7°, 14.9°, 15.4°, 15.8°, 16.7°, 18.9° unique |
| DVS | FIG. 4;<br>hygroscopic;<br>adsorption transition at about 60% RH;<br>adsorbs about 3.8 wt %;<br>deliquescent above 90% RH;<br>crystalline form changes to Form III after cycle. | FIG. 8;<br>hygroscopic;<br>adsorption transition at about 40% RH;<br>adsorbs about 3.8 wt %;<br>deliquescent above 90% RH;<br>crystalline form changes to Form III after cycle | FIG. 12;<br>non-hygroscopic;<br>adsorption of less than 0.5% at 90% RH;<br>deliquescent above 95% RH;<br>no change in crystalline form after cycle. |
| habit | granular | rods | needle/rods($CH_2Cl_2$/hexanes)<br>thin-plates (toluene/MeOH)<br>block (cyclohexane/IPA) |

The absence of weight loss below 150° C. in the TGA data suggests that both Forms I and II are anhydrous, non-solvated crystal forms. This result is in contrast with Form III which displays a dehydration feature calculated as a 3.7% weight loss which is consistent with the theoretical weight loss of 3.7% for a hemihydrate. Analysis by DSC further confirms the TGA results, where only Form III shows a dehydration event at about 95° C. The individual DSC traces further reveal a melting/decomposition endotherm at about 200-201° C. for each of the three forms.

DVS data for each of the three crystal forms reveals the hygroscopic nature of both Forms I and II, which readily adsorb moisture at RH greater than about 40-60% RH. In addition, both Forms I and II were calculated to adsorb about 3.8 wt % moisture between about 40 and about 80% RH which is consistent with conversion to the hemihydrate (Form III). XRPD carried out on both Forms I and II after the DVS cycle confirmed this conversion. In contrast, the DVS data in connection with Form III shows that it is substantially non-hygroscopic, adsorbing less than 0.5 wt % water at 90% RH and the XRPD pattern showed no change in crystalline form after the DVS cycle.

X-ray powder diffraction data for each of the three forms reveal similar patterns. In fact, the diffraction patterns of Forms I and II share essentially the same peaks, except that Form II has at least one unique peak at about 11.4° (2θ) which is not substantially present in diffraction patterns of Form I. Because both Forms I and II are hygroscopic, diffraction patterns obtained for these forms were often combined with peaks from the hemihydrate, Form III. The diffraction pattern of Form III differs significantly from the diffraction patterns of both Forms I and II, having several unique peaks. Exemplary peaks unique to Form III are set out in Table 1 above. X-ray powder diffraction peaks for each of the three forms are compared in Table 2 below.

TABLE 2

| Form I degrees (2θ) | Form II degrees (2θ) | Form III degrees (2θ) |
|---|---|---|
| 6.5 | 6.5 | 10.2 |
| 9.6 | 9.6 | 12.7 |
| 10.2 | 10.2 | 13.7 |
| 12.9 | 11.4 | 14.9 |
| 17.1 | 12.9 | 15.4 |
| 17.5 | 17.1 | 15.8 |
| 17.8 | 17.5 | 16.7 |
| 18.5 | 17.8 | 18.5 |
| 19.5 | 18.5 | 18.9 |
| 19.8 | 19.5 | 19.2 |
| 20.1 | 19.8 | 20.1 |
| 20.5 | 20.1 | 20.5 |
| 21.3 | 20.5 | 21.4 |
| 21.6 | 21.3 | 22.8 |
| 22.3 | 21.6 | 23.2 |
| 23.7 | 22.3 | 23.5 |
| 24.6 | 23.7 | 24.0 |
| 25.3 | 24.6 | 24.2 |
| 25.9 | 25.3 | 24.7 |
| 27.6 | 25.9 | 25.3 |
| 27.9 | 27.6 | 25.7 |
| 28.3 | 27.9 | 26.0 |
| 28.7 | 28.3 | 26.5 |
| 29.5 | 28.7 | 26.9 |
| 29.8 | 29.5 | 27.6 |
| 30.3 | 29.8 | 28.2 |
| 30.9 | 30.3 | 29.0 |
| 31.3 | 30.9 | 30.0 |
| 32.6 | 31.3 | 30.3 |
| 32.9 | 32.6 | 30.8 |
|  | 32.9 | 31.1 |
|  |  | 32.0 |
|  |  | 32.3 |
|  |  | 32.7 |
|  |  | 33.3 |
|  |  | 33.8 |
|  |  | 35.8 |

Hemihydrate

In a first aspect of the invention, the present invention provides a compound which is (R)-8-chloro-1-methyl-2,3,4,5-tetrahydro-1H-3-benzazepine hydrochloride hemihydrate.

In some embodiments, the hemihydrate has an X-ray powder diffraction pattern characteristic of Form III comprising peaks, in tennis of 2θ, at about 13.7° and about 14.9°. In further embodiments, the hemihydrate has an X-ray powder diffraction pattern comprising peaks, in terms of 2θ, at about 13.7°, about 14.9°, about 15.4°, about 15.8°, and about 16.7°.

Figure 11:
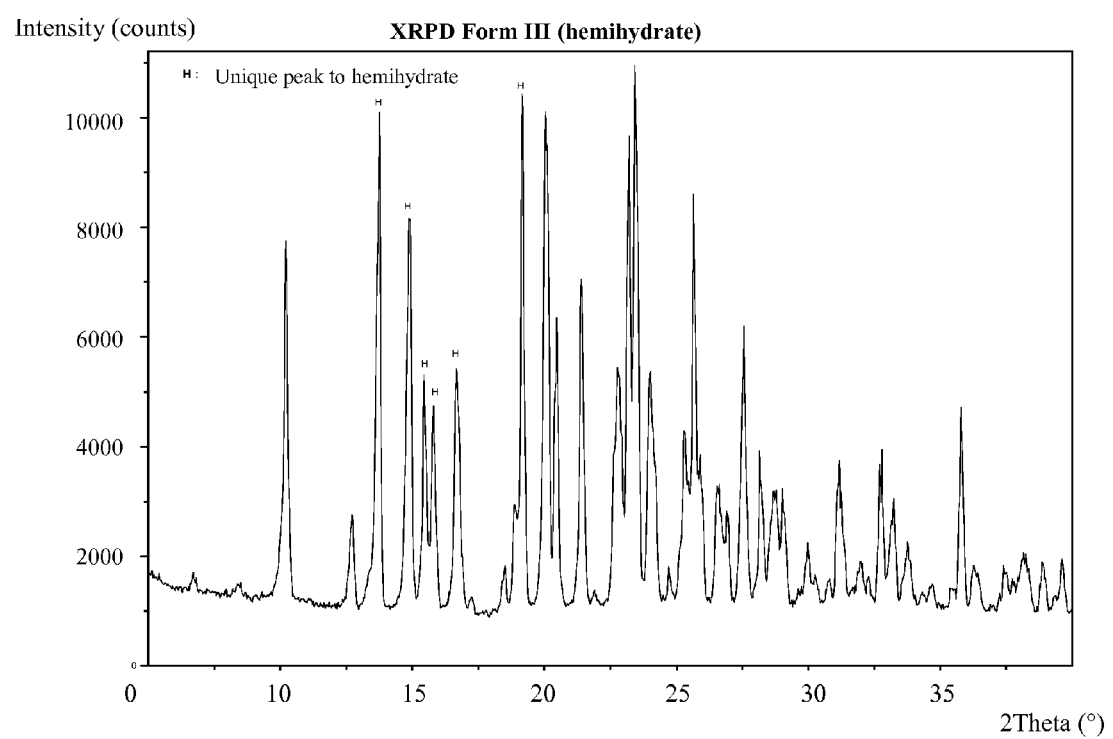
FIG. 11 depicts a powder X-ray diffraction pattern (XRPD) for a sample containing crystalline Form III (PANalytical X'Pert Plus Powder X-Ray Diffractometer; 5.0°-50.0° 2θ).

In yet further embodiments, the hemihydrate has an X-ray powder diffraction pattern comprising peaks, in terms of 2θ, at about 13.7°, about 14.9°, about 15.4°, about 15.8°, about 16.7°, about 20.1°, or about 21.4°. In yet further embodiments, the hemihydrate has an X-ray powder diffraction pattern substantially as shown in FIG. 11, wherein by "substantially" is meant that the reported peaks can vary by about ±0.2°.

Figure 10:
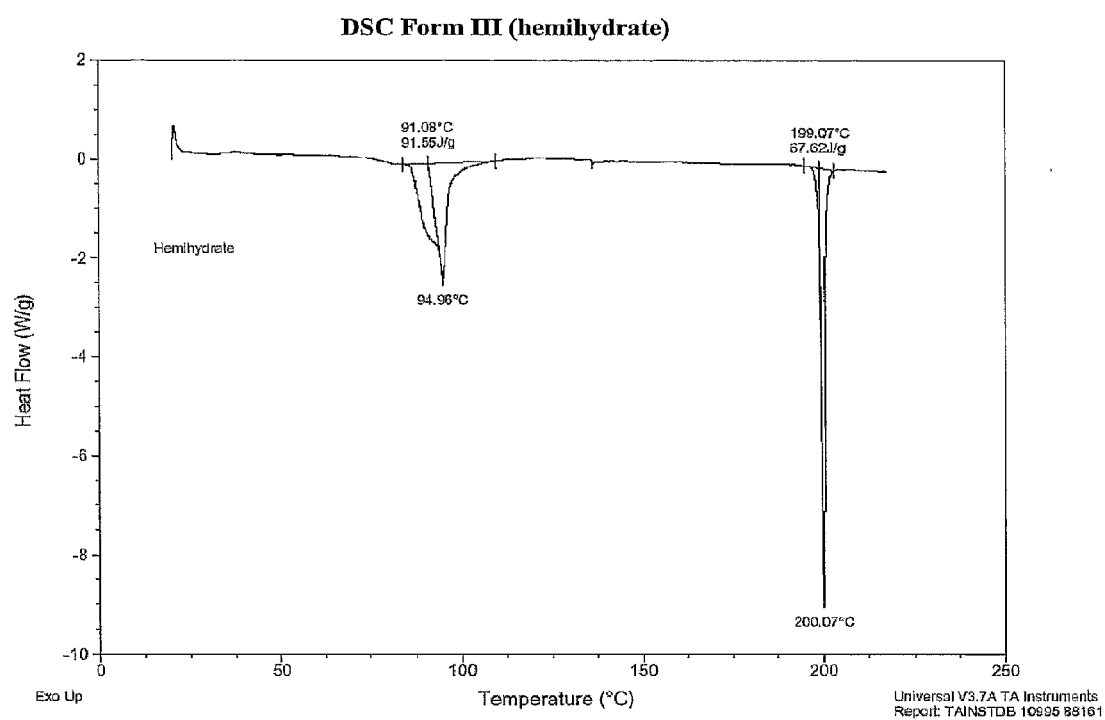
FIG. 10 depicts a differential scanning calorimetry (DSC) thermogram for crystalline Form III of the invention (TA Instruments DSC Q1000; 25-220° C.; 10° C./min).

In some embodiments, the hemihydrate has a differential scanning calorimetry trace comprising a relatively broad dehydration endotherm at about 90 to about 110° C. (e.g., about 95° C.). In addition, the differential scanning calorimetry trace comprises a further endotherm at about 200° C. In yet further embodiments, the hemihydrate has a differential scanning calorimetry trace substantially as shown in FIG. 10, wherein by "substantially" is meant that the reported DSC feature can vary by about ±4°.

In some embodiments, the hemihydrate has a crystal habit which is rods, thin-plates, blocks, or a mixture thereof.

Figure 8:
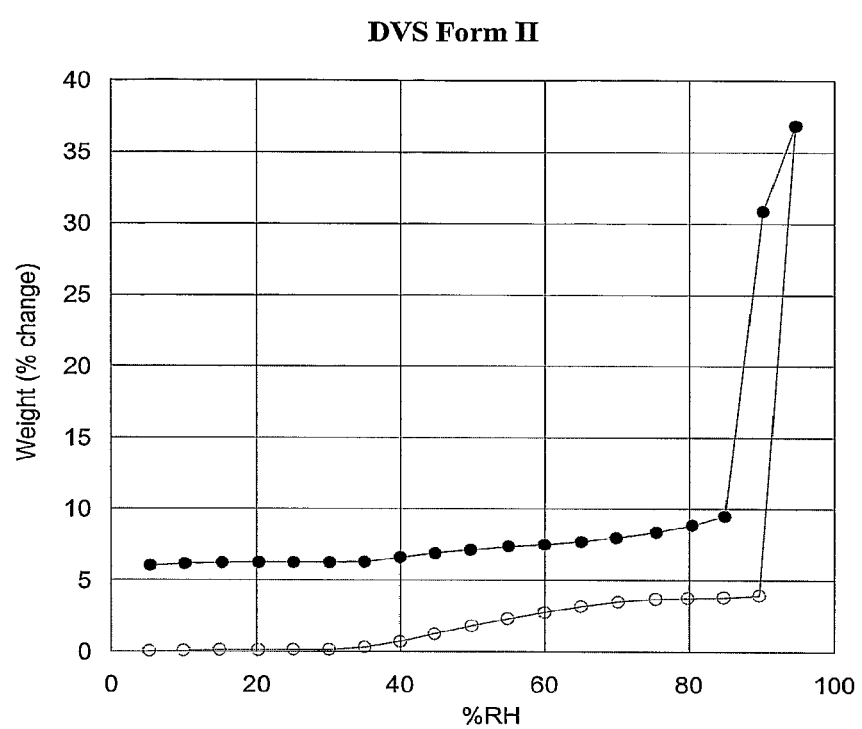
FIG. 8 depicts a dynamic vapor sorption (DVS) scan for crystalline Form II of the invention (VTI dynamic vapor desorption analyzer).
Figure 9:
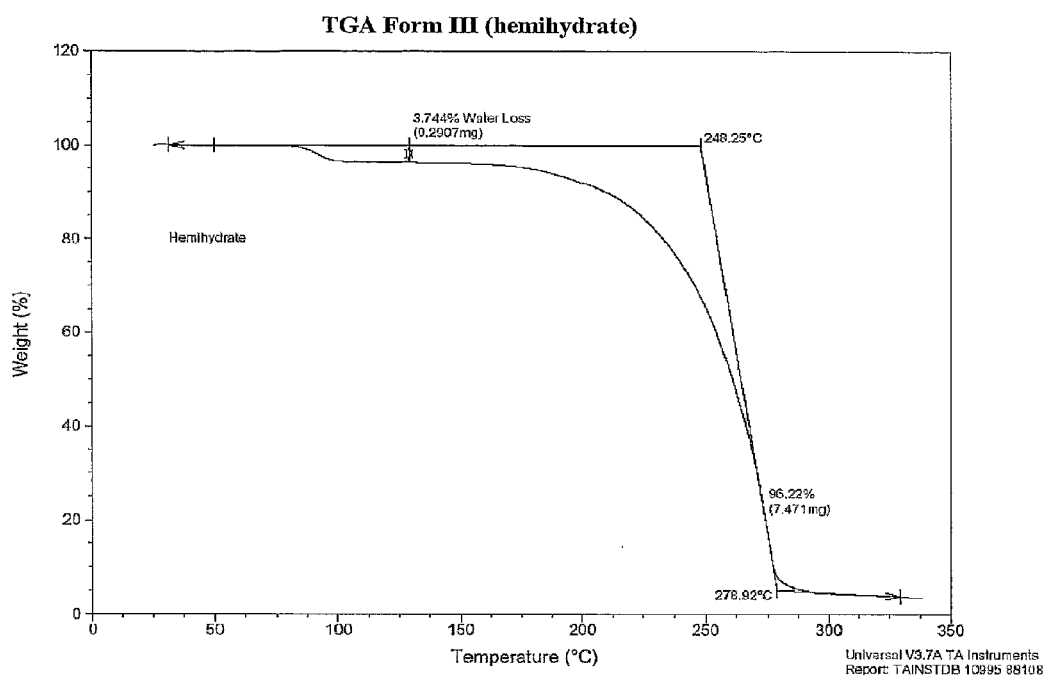
FIG. 9 depicts a thermogravimetric analysis (TGA) thermogram for crystalline Form III of the invention (TA Instruments TGA Q500 in open cell open cell; 25-350° C.; 10° C./min).

In some embodiments, the hemihydrate has a dynamic vapor sorption profile substantially as shown in FIG. 8, wherein by "substantially" is meant that the reported DVS features can vary by about ±5% RH.

In some embodiments, the hemihydrate has a thermogravimetric analysis profile showing about 3.7% weight loss corresponding to loss of water. In further embodiments, the hemihydrate has a thermogravimetric analysis profile substantially as shown in FIG. 9, wherein by "substantially" is meant that the reported TGA features can vary be about ±5° C.

The hemihydrate can be prepared by any of the suitable procedures known in the art for preparing hydrates of compounds. In some embodiments, the hemihydrate can be prepared by at least partially dissolving (R)-8-chloro-1-methyl-2,3,4,5-tetrahydro-1H-3-benzazepine hydrochloride in a crystallizing solvent containing water, and inducing precipitation of the hemihydrate from the crystallizing solvent.

The crystallizing solvent can be any solvent or mixture of solvents that at least partially dissolves (R)-8-chloro-1-methyl-2,3,4,5-tetrahydro-1H-3-benzazepine hydrochloride and contains water. In some embodiments, the crystallizing solvent contains an alcohol, water, and a hydrocarbon. Suitable alcohols include, for example, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the alcohol is isopropanol (2-propanol). Suitable hydrocarbons include, for example, benzene, cyclohexane, pentane, hexane, toluene, cycloheptane, methylcyclohexane, heptane, ethylbenzene, m-, o-, or p-xylene, octane, indane, nonane, or naphthalene. In some embodiments, the hydrocarbon is cyclohexane.

In some embodiments, the weight ratio of alcohol to water in the crystallizing solvent is about 35:1 to about 25:1, about 32:1 to about 27:1, or about 30:1 to about 28:1. In some embodiments, the weight ratio of alcohol to water is about 29:1. In some embodiments, the weight ratio of alcohol plus water to hydrocarbon in the crystallizing solvent is about 5:1 to about 2:1, about 3:1 to about 2:1, or about 2.5:1. In some embodiments, the weight ratio of (R)-8-chloro-1-methyl-2,3,4,5-tetrahydro-1H-3-benzazepine hydrochloride to crystallizing solvent (e.g., alcohol plus water plus hydrocarbon) is about 1:2 to about 1:15, about 1:6 to about 1:10, or about 1:8.

In some embodiments, the mixture containing the crystallizing solvent and (R)-8-chloro-1-methyl-2,3,4,5-tetrahydro-1H-3-benzazepine hydrochloride is maintained at and/or heated to a temperature of about 40 to about 80, about 50 to about 70, or about 60° C. prior to inducing precipitation.

In some embodiments, the (R)-8-chloro-1-methyl-2,3,4,5-tetrahydro-1H-3-benzazepine hydrochloride is substantially dissolved in the crystallizing solvent prior to inducing precipitation. Substantial dissolution can be achieved by heating the mixture to a suitable temperature such as between about 40 and about 80° C. (e.g., about 60° C.).

Precipitation of the hemihydrate product can be induced by cooling the mixture containing the crystallizing solvent and (R)-8-chloro-1-methyl-2,3,4,5-tetrahydro-1H-3-benzazepine hydrochloride. In some embodiments, the mixture is cooled to a temperature of about −15 to about 15° C. In some embodiments, the mixture is cooled to a temperature of about −5 to about 10° C. In further embodiments, the mixture is cooled to a temperature of about 0 to about 5° C.

Figure 12:
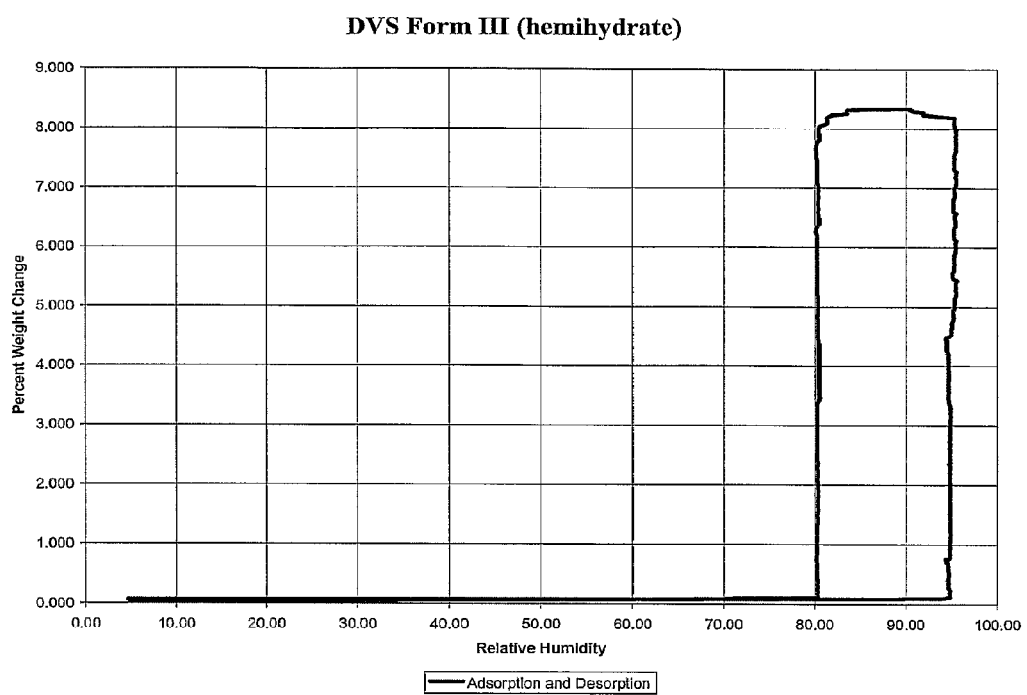
FIG. 12 depicts a dynamic vapor sorption (DVS) scan for crystalline Form III of the invention.

In some embodiments, the present invention provides a compound which is (R)-8-chloro-1-methyl-2,3,4,5-tetrahydro-1H-3-benzazepine hydrochloride or hydrate thereof, wherein the compound or hydrate thereof gains less than about 1.0%, less than about 0.5%, or less than about 0.2% weight after undergoing a dynamic vapor sorption cycle. The weight gain (if any) can be measured as the difference between the sample weight at the beginning of the cycle and at the end of the cycle. These two points typically occur at or near the same relative humidity (RH) value. For example, a cycle might be started at about 0% RH to about 20% RH, run to about 85% to about 100% RH, and then returned to the starting RH point. In some embodiments, weight gain is measured at a starting/ending point of about 5% RH, 10% RH, or 15% RH. In some embodiments, the cycle is runs through a maximum RH of about 85%, about 90%, about 95%, or about 100%. In some embodiments, the sample shows weight gain of more than about 1%, more than about 2%, or more than about 5% during the cycle at about 80% or greater RH. In some embodiments, the present invention provides a compound which is (R)-8-chloro-1-methyl-2,3,4,5-tetrahydro-1H-3-benzazepine hydrochloride or hydrate thereof having a dynamic vapor sorption profile substantially as shown in FIG. 12.

Form I

Figure 3:
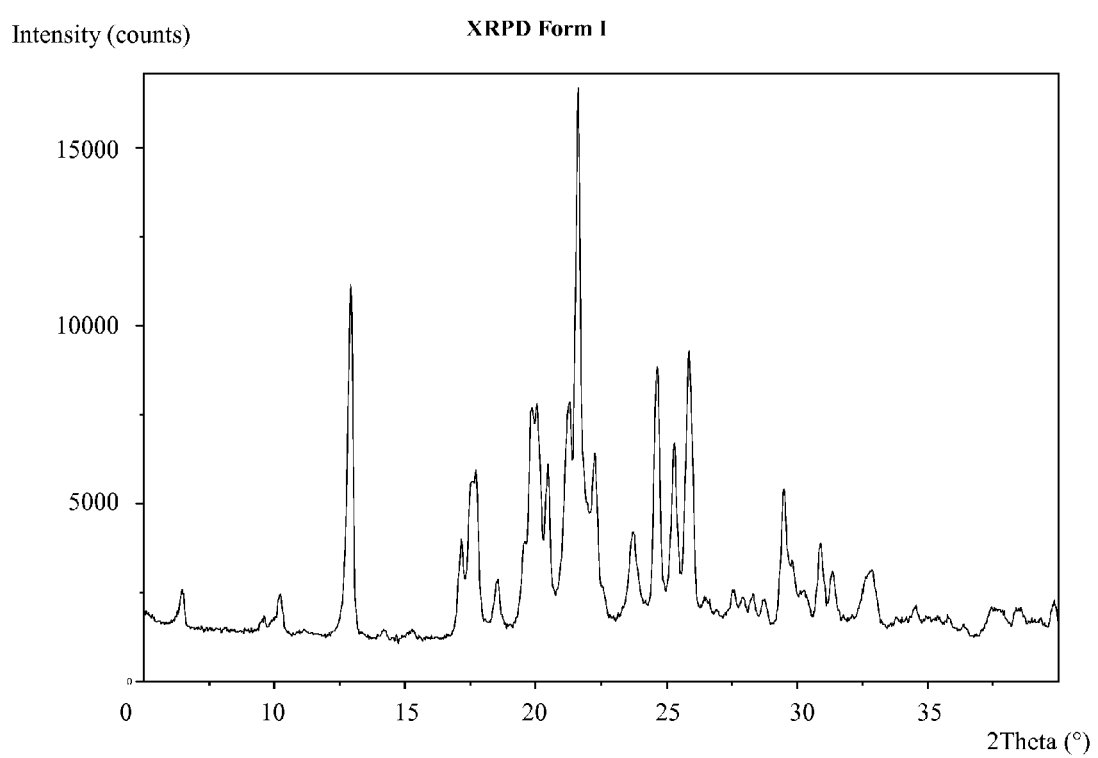
FIG. 3 depicts a powder X-ray diffraction pattern (XRPD) for a sample containing crystalline Form I (PANalytical X'Pert Plus Powder X-Ray Diffractometer; 5.0°-50.0° 2θ).

In a second aspect, the present invention is directed to a crystalline form of (R)-8-chloro-1-methyl-2,3,4,5-tetrahydro-1H-3-benzazepine hydrochloride (Form I) having an X-ray powder diffraction pattern comprising peaks, in terms of 2θ, at about 6.5°, about 9.6°, and about 10.2°. In some embodiments, the crystalline form has an X-ray powder diffraction pattern comprising peaks, in terms of 2θ, at about 6.5°, about 9.6°, about 10.2°, about 12.9, about 17.1°, about 17.5°, and about 17.8°. In further embodiments, the crystalline form has an X-ray powder diffraction pattern comprising peaks, in terms of 2θ, at about 6.5°, about 9.6°, about 10.2°, about 12.9, about 17.1°, about 17.5°, about 17.8°, about 18.5°, about 19.5°, and about 19.8°. In yet further embodiments, the crystalline form has an X-ray powder diffraction pattern comprising substantially no peak (e.g., where intensity is less than about 5% of the most intense peak) at about 10.5° to about 11.5°. In yet further embodiments, the crystalline form has an X-ray powder diffraction pattern comprising substantially no peak at about 11.4°. In yet further embodiments, the crystalline form has an X-ray powder diffraction pattern substantially as shown in FIG. 3, wherein by "substantially" is meant that the reported peaks can vary by about ±0.2°.

In some embodiments, the crystalline form has a differential scanning calorimetry trace comprising an endotherm at about 201° C. In further embodiments, the crystalline form has a differential scanning calorimetry trace substantially as shown in FIG. 2, wherein by "substantially" is meant that the reported DSC features can vary by about ±4°.

In some embodiments, the crystalline form has a crystal habit which is granular.

Figure 4:
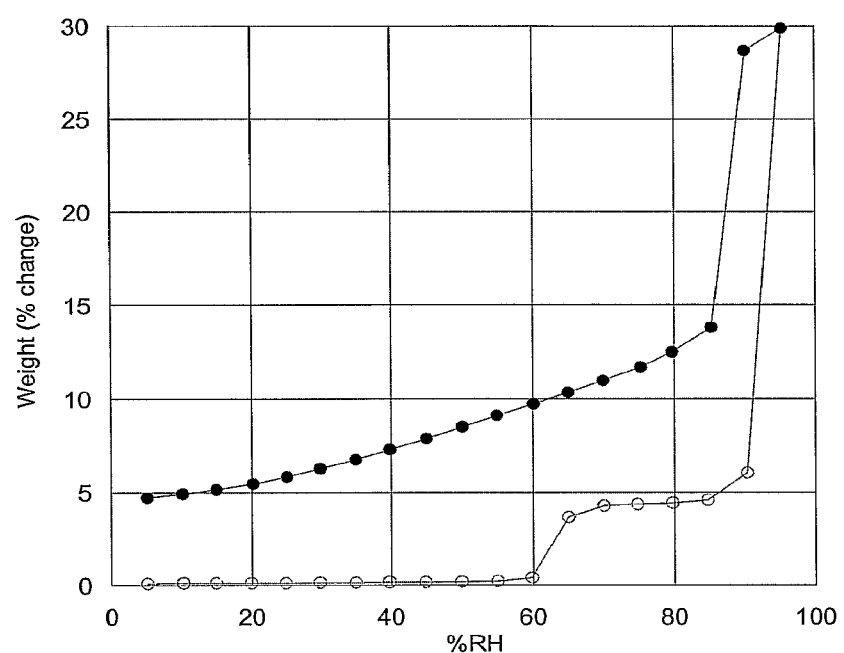
FIG. 4 depicts a dynamic vapor sorption (DVS) scan for crystalline Form I of the invention (VTI dynamic vapor desorption analyzer).

In some embodiments, the crystalline form has a dynamic vapor sorption profile substantially as shown in FIG. 4, wherein by "substantially" is meant that the reported DVS features can vary by about +5% RH.

Figure 2:
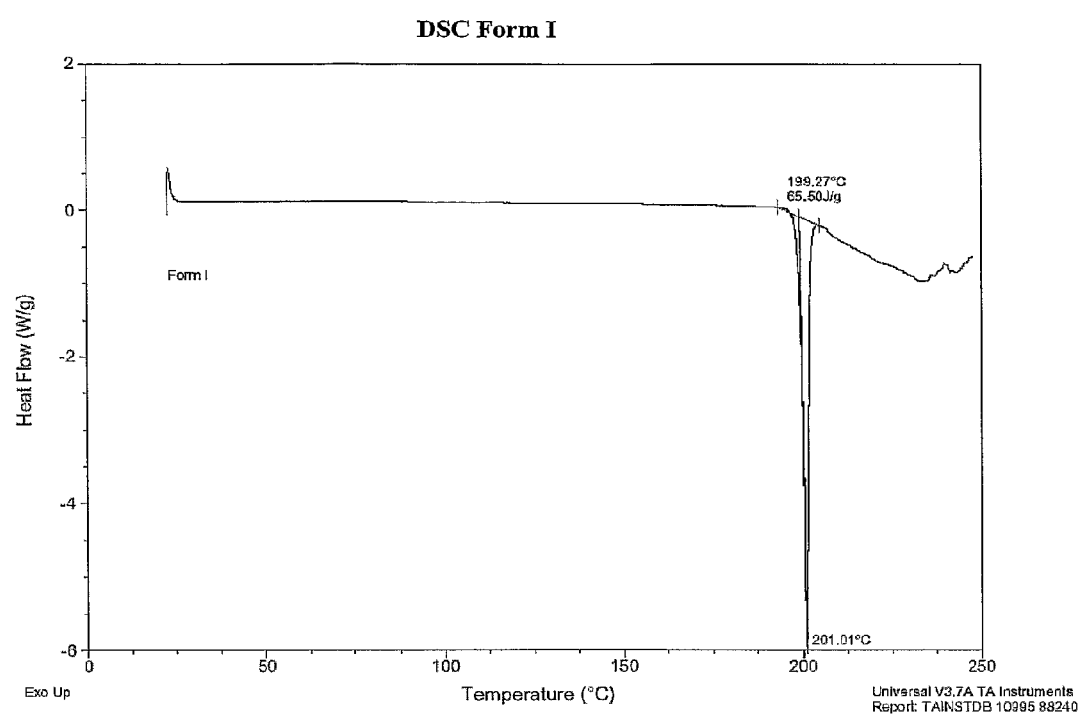
FIG. 2 depicts a differential scanning calorimetry (DSC) thermogram for crystalline Form I of the invention (TA Instruments DSC Q1000; 25-220° C.; 10° C./min).

In some embodiments, the crystalline form has a thermogravimetric analysis profile substantially as shown in FIG. 1, wherein by "substantially" is meant that the reported TGA features can vary be about ±5° C.

Form I can be prepared by any of the suitable procedures known in the art for preparing crystalline polymorphs. In some embodiments, Form I can be prepared by heating crystalline (R)-8-chloro-1-methyl-2,3,4,5-tetrahydro-1H-3-benzazepine hydrochloride, where the crystalline (R)-8-chloro-1-methyl-2,3,4,5-tetrahydro-1H-3-benzazepine hydrochloride contains one or more crystalline forms other than Form I. For example, Form I can be prepared by heating samples containing Forms II or III (hemihydrate), or mixtures thereof. In some embodiments, Forms II or III or mixtures thereof, can be heated to a temperature of at least about 60° C. for time and under conditions suitable for forming Form I. In some embodiments, Forms II or III or mixtures thereof can be heated to at temperature of at least about 60° C. for at least about 2 hours.

Form II

Figure 7:
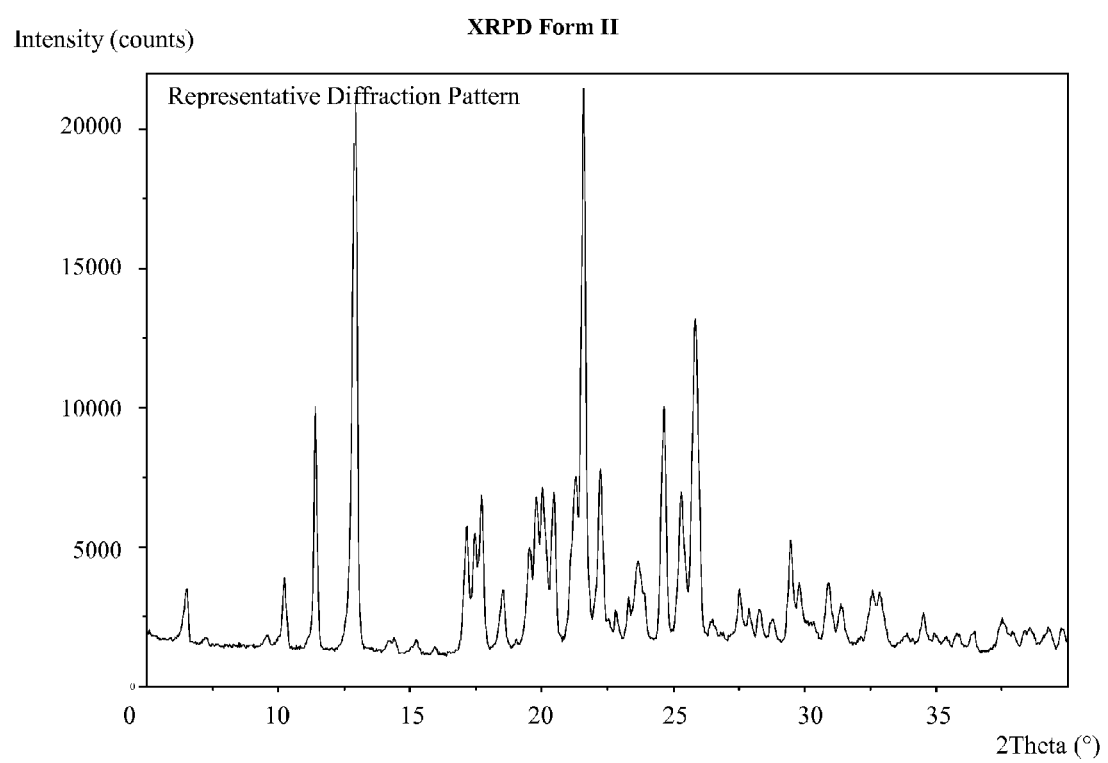
FIG. 7 depicts a powder X-ray diffraction pattern (XRPD) for a sample containing crystalline Form II (PANalytical X'Pert Plus Powder X-Ray Diffractometer; 5.0°-50.0° 2θ).

In a third aspect of the invention, the invention provides a crystalline form of (R)-8-chloro-1-methyl-2,3,4,5-tetrahydro-1H-3-benzazepine hydrochloride (Form II) having an X-ray powder diffraction pattern comprising at least one peak, in terms of 2θ, at about 11.4°. In some embodiments, the crystalline form has an X-ray powder diffraction pattern comprising peaks, in terms of 2θ, at about 6.5°, about 9.6°, about 10.2°, and about 11.4°. In some embodiments, the crystalline form has an X-ray powder diffraction pattern comprising peaks, in terms of 2θ, at about 6.5°, about 9.6°, about 10.2°, about 11.4°, about 12.9°, about 17.1°, about 17.5°, and about 17.7°. In some embodiments, the crystalline form has an X-ray powder diffraction pattern comprising peaks, in terms of 2θ, at about 6.5°, about 9.6°, about 10.2°, about 11.4°, about 12.9, about 17.1°, about 17.5°, about 17.8°, about 18.5°, about 19.5°, and about 19.8°. In some embodiments, the crystalline form has an X-ray powder diffraction pattern substantially as shown in FIG. 7, wherein by "substantially" is meant that the reported peaks can vary by about ±0.2°.

Figure 6:
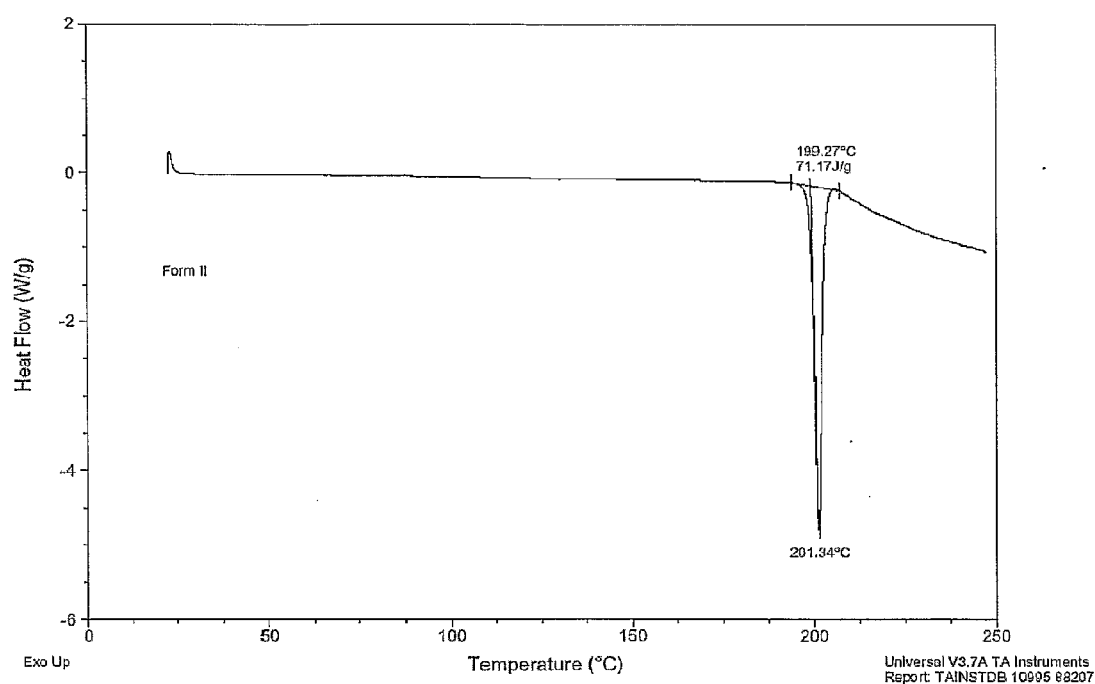
FIG. 6 depicts a differential scanning calorimetry (DSC) thermogram for crystalline Form II of the invention (TA Instruments DSC Q1000; 25-220° C.; 10° C./min).

In some embodiments, Form II has a differential scanning calorimetry trace comprising an endotherm at about 201° C. In further embodiments, Form I has a differential scanning calorimetry trace substantially as shown in FIG. 6, wherein by "substantially" is meant that the reported DSC feature can vary by about ±4° C.

In some embodiments, Form II has a crystal habit which is rods.

In some embodiments, Form II has a dynamic vapor sorption profile substantially as shown in FIG. 8, wherein by "substantially" is meant that the reported DVS features can vary by about ±5% RH.

Figure 5:
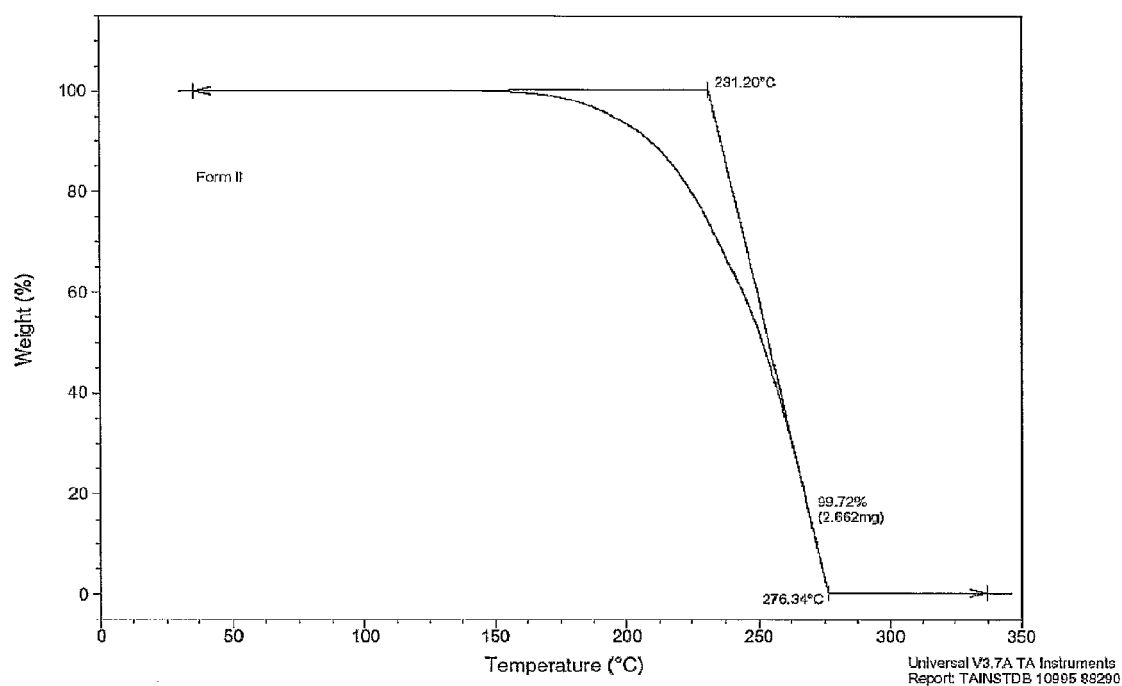
FIG. 5 depicts a thermogravimetric analysis (TGA) thermogram for crystalline Form II of the invention (TA Instruments TGA Q500 in open cell open cell; 25-350° C.; 10° C./min).

In some embodiments, Form II has a thermogravimetric analysis profile substantially as shown in FIG. 5, wherein by "substantially" is meant that the reported TGA features can vary be about ±5° C.

Form II can be prepared by any of the suitable procedures known in the art for preparing crystalline polymorphs. For example, Form II can be prepared by dissolving (R)-8-chloro-1-methyl-2,3,4,5-tetrahydro-1H-3-benzazepine hydrochloride in an anhydrous crystallizing solvent and inducing precipitation such as by cooling or addition of anti-solvent. In some embodiments, Form II can be prepared by combining (R)-8-chloro-1-methyl-2,3,4,5-tetrahydro-1H-3-benzazepine (free base) in a hydrocarbon solvent to form a mixture; optionally removing water from the mixture to form a dehydrated mixture; and adding HCl and alcohol to the dehydrated mixture. Suitable alcohols and hydrocarbon solvents are listed hereinabove. In some embodiments, the hydrocarbon solvent is cyclohexane. In further embodiments, the alcohol is isopropanol. In some embodiments, addition of the alcohol is carried out over the time period of about 15 minutes to about 2 hours. In some embodiments, the weight ratio of (R)-8-chloro-1-methyl-2,3,4,5-tetrahydro-1H-3-benzazepine to cyclohexane is about 1:20 to about 1:10, about 1:17 to about 1:12, or about 1:10 to about 1:5, or about 1:7 to about 1:8. In further embodiments, the weight ratio of (R)-8-chloro-1-methyl-2,3,4,5-tetrahydro-1H-3-benzazepine to alcohol is about 1:1 to about 1:10 about 1:2 to about 1:5, or about 1:3.

Removal of water from the solvent mixture can be carried out by any of routine methods in the art such as by incubation with molecular sieves or by azeotropic distillation. Final water content of the mixture after removing water can be less than about 0.1, preferably less than about 0.05, or more preferably less than about 0.03 wt %. If the water content of the solvent mixture is sufficiently low (e.g., less than about 0.1 wt %), the water removal step can be omitted.

During the formation of the salt, the HCl (e.g., HCl gas) can be added in molar excess relative to (R)-8-chloro-1-methyl-2,3,4,5-tetrahydro-1H-3-benzazepine.

Compositions

The present invention further provides compositions containing one or more of the three crystal forms of (R)-8-chloro-1-methyl-2,3,4,5-tetrahydro-1H-3-benzazepine hydrochloride. In some embodiments, the compositions of the invention include at least about 50, about 60, about 70, about 80, about 90, about 95, about 96, about 97, about 98, or about 99% by weight of the hemihydrate (e.g., Form III). In some embodiments, the compositions of the invention include at least about 50, about 60, about 70, about 80, about 90, about 95, about 96, about 97, about 98, or about 99% by weight of Form I. In some embodiments, the compositions of the invention include at least about 50, about 60, about 70, about 80, about 90, about 95, about 96, about 97, about 98, or about 99% by weight of Form II. In some embodiments, the compositions of the invention contain a mixture of two or more of Forms I, II, and III. In some embodiments, compositions of the invention include Form I, Form II or the hemihydrate and a pharmaceutically acceptable carrier.

Methods

The crystal forms of the invention have activity as 5-HT$_{2C}$ receptor agonists. Accordingly, the crystal forms of the invention can be used in methods of agonizing (e.g., stimulating, increasing activity of, etc.) the 5-HT$_{2C}$ receptor by contacting the receptor with any one or more of the crystal forms, or compositions thereof, described herein. In further embodiments, the crystal forms of the invention can be used to agonize 5-HT$_{2C}$ receptors in an individual in need of such agonizing by administering a therapeutically effective amount of a crystal form of the invention.

The present invention further provides methods of treating diseases associated with the 5-HT$_{2C}$ receptor in an individual (e.g., patient) by administering to the individual in need of such treatment a therapeutically effective amount or dose of a crystal form of the present invention or a pharmaceutical composition thereof. Example diseases can include any disease, disorder or condition that is directly or indirectly linked to expression or activity of the 5-HT$_{2C}$ receptor, including under-expression or abnormally low activity of the 5-HT$_{2C}$ receptor.

Example diseases include disorders of the central nervous system; damage to the central nervous system; cardiovascular disorders; gastrointestinal disorders; diabetes insipidus, and sleep apnea. Example disorders of the central nervous system include depression, atypical depression, bipolar disorders, anxiety disorders, obsessive-compulsive disorders, social phobias or panic states, sleep disorders, sexual dysfunction, psychoses, schizophrenia, migraine and conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension.

The present invention further provides methods of decreasing food intake of a mammal by administering a therapeutically effective amount of a crystal form of the invention.

The present invention further provides methods for inducing satiety in a mammal by administering a therapeutically effective amount of a crystal form of the invention.

The present invention further provides methods for controlling weight gain of a mammal by administering a therapeutically effective amount of a crystal form of the invention.

The present invention further provides methods of treating obesity by administering to a patient a therapeutically effective amount of a crystal form of the invention.

In some embodiments, the above methods further comprise the step of identifying a patient, where the patient is in need of treatment for the particular disease being treated, wherein the identifying step is performed prior to administration to the patient of the therapeutically effective amount of the crystal form of the invention.

As used herein, the term "treating" refers to, for example, preventing, inhibiting, as well as ameliorating a disease, condition or disorder in an individual.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting further development of the pathology and/or symptomatology) such as stabilizing viral load in the case of a viral infection; and (3) ameliorating the disease; for example, ameliorating a disease, condition or disorder in an individual that is experiencing or displaying the pathology or symptomatology of the disease, condition or disorder (i.e., reversing the pathology and/or symptomatology) such as lowering viral load in the case of a viral infection.

Pharmaceutical Formulations and Dosage Forms

When employed as pharmaceuticals, the crystal forms of the invention can be administered in the form of pharmaceutical compositions. These compositions can be administered by a variety of routes including oral, rectal, transdermal, topical, subcutaneous, intravenous, intramuscular, and intranasal, and can be prepared in a manner well known in the pharmaceutical art.

This invention also includes pharmaceutical compositions which contain, as the active ingredient, one or more of the crystal forms of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the crystal form can be milled to provide the appropriate particle size prior to combining with the other ingredients. If the crystal form is substantially insoluble, it can be milled to a particle size of less than 200 mesh. If the crystal form is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The crystal form can be effective over a wide dosage range and is generally administered in a therapeutically effective amount. It will be understood, however, that the amount of the crystal form actually administered will usually be determined by a physician, according to the relevant circumstances, including the condition to be treated, the chosen route of administration, the actual crystal form administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a crystal form of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the crystal forms and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of crystal form or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the crystal forms of the present invention can vary according to, for example, the particular use for which the treatment is made, the manner of administration of the crystal form, the health and condition of the patient, and the judgment of the prescribing physician. The proportion or concentration of a crystal form of the invention in a pharmaceutical composition can vary depending upon a number of factors including dosage, chemical characteristics (e.g., hydrophobicity), and the route of administration. For example, the crystal forms of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the crystal form selected, formulation of the excipient, and its route of administration. Effective doses can be extrapolated from dose-response curves derived from in vitro or animal model test systems.

The crystal forms of the invention can also be formulated in combination with one or more additional active ingredients which can include any pharmaceutical agent such as antiviral agents, antibodies, immune suppressants, anti-inflammatory agents and the like.

In order that the invention disclosed herein may be more efficiently understood, examples are provided below. It should be understood that these examples are for illustrative purposes only and are not to be construed as limiting the invention in any manner.

EXAMPLES

Example 1

Preparation of Hydrochloric Acid Salt of (R)-8-chloro-1-methyl-2,3,4,5-tetrahydro-1H-3-benzazepine To a clean, dry 25 mL round bottom flask were added (R)-8-chloro-1-methyl-2,3,4,5-tetrahydro-1H-3-benzazepine free amine (220 mg), 3 mL methylene chloride, and 1.74 mL of 1M HCl in ether. The mixture was stirred for 5 minutes at room temperature. The solvent was removed under reduced pressure to give a white solid, the HCl salt. The salt was re-dissolved in methylene chloride (3 mL) and an additional 1.74 mL of 1 M HCl was added and the solution was again stirred at room temperature for 5 minutes. The solvent was removed under reduced pressure to give the desired HCl salt of (R)-8-chloro-1-methyl-2,3,4,5-tetrahydro-1H-3-benzazepine (190 mg crude weight, 95% yield). NMR data was consistent with the desired product.

$^1$H NMR (CDCl$_3$): 10.2 (br s, 1H), 9.8 (br s, 1H), 7.14 (dd, 1H, J=2, 8 Hz), 7.11 (d, 1H, J=2 Hz), 7.03 (d, 1H, J=8 Hz), 3.6 (m, 2H), 3.5 (m, 2H), 2.8-3.0 (m, 3H), 1.5 (d, 3H, J=7 Hz).

Example 2

Preparation of (R)-8-chloro-1-methyl-2,3,4,5-tetrahydro-1H-3-benzazepine hydrochloride Hemihydrate (Form III)

At 20 to 25° C., 160 g, 689 mM of (R)-8-chloro-1-methyl-2,3,4,5-tetrahydro-1H-3-benzazepine hydrochloride is treated under a nitrogen atmosphere with 359.36 g of isopropanol. The resulting mixture is heated to 60° C. providing a clear solution. After the desired temperature is reached, 12.43 g of water are added followed by 960 g of cyclohexane which are added at 60 to 40° C. Afterwards the solution is cooled over 2 hours with slow stirring (at 160 rpm) to 20 to 25° C. After crystallization of the product is observed the resulting suspension is cooled to 0 to 5° C. and stirred afterwards for additional 3 h at 0 to 5° C. The suspension is filtered and the filter cake is washed with 160 g of cyclohexane via the reactor and further 160 g of cyclohexane. From this process 176.81 g of a colorless wet product was obtained, which was dried at 35 to 45° C., preferentially 40° C., at 50 mbar, 153.03 g (95.3 weight %) of (R)-8-chloro-1-methyl-2,3,4,5-tetrahydro-1H-3-benzazepine hydrochloride hemihydrate was obtained as a colorless crystalline solid.

Example 3

Preparation of (R)-8-chloro-1-methyl-2,3,4,5-tetrahydro-1H-3-benzazepine hydrochloride Crystalline Form II Approximately 6.6 g of the free base (R)-8-chloro-1-methyl-2,3,4,5-tetrahydro-1H-3-benzazepine was dissolved in cyclohexane to a volume of about 130 mL. The water content was reduced by azeotropic distillation to a level of less than 0.03%. Further cyclohexane was charged to the flask as required to maintain the same volume. The clear solution was filtered and a mixture of 3.06 g, 83.9 mmol hydrochloric acid gas and 19.38 g isopropanol was added over 60 min at an internal temperature 20° C. The resulting suspension was stirred for at least 2 h, before being filtered. The filter cake was washed with 60 g of acetone cooled to 0-10° C. and the product (9.19 g) was dried at 60° C. at 30 mbar to provide 5.88 g of Form II.

Example 4

Preparation of (R)-8-chloro-1-methyl-2,3,4,5-tetrahydro-1H-3-benzazepine hydrochloride Crystalline Form I Form I was prepared by heating a sample of either Form II (e.g., prepared according to Example 2) or Form III (e.g., prepared according to Example 1) to a temperature of about 160° C. in a TGA furnace for about 15 min when heated at a rate of about 10° C./min. Conversion to Form I was detected by XRPD analysis.

Example 5

Stability of (R)-8-chloro-1-methyl-2,3,4,5-tetrahydro-1H-3-benzazepine hydrochloride Crystalline Form I A sample of Form I was heated to 160° C. in a TGA furnace for about 15 min when heated at a rate of about 10° C./min. XRPD analysis showed no change in crystal form after heating.

Example 6

Heat Stability of (R)-8-chloro-1-methyl-2,3,4,5-tetrahydro-1H-3-benzazepine hydrochloride Crystalline Form III A sample of Form III was heated to 60° C. for at least 2 hours. XRPD analysis showed substantially no change in crystal form after heating.

A sample of Form III was heated to 60° C. for one day. XRPD analysis showed partial conversion to Form I after heating.

A sample of Form III was heated to 80° C. for 30 minutes. XRPD analysis showed partial conversion to Form I after heating.

A sample of Form III was heated to 80° C. for 1 day. XRPD analysis showed partial conversion to Form I after heating.

Various modifications of the invention, in addition to those described herein, will be apparent to those skilled in the art from the foregoing description. Such modifications are also intended to fall within the scope of the appended claims. Each reference, including all patents, patent applications, and journal literature, cited in the present application is incorporated herein by reference in its entirety.

What is claimed is:

1. A method of treatment of obesity comprising administering to an individual in need of such treatment a therapeutically effective amount of (R)-8-chloro-1-methyl-2,3,4,5-tetrahydro-1H-3-benzazepine hydrochloride hemihydrate.

2. A method of decreasing food intake comprising administering to an individual in need of such administration a therapeutically effective amount of (R)-8-chloro-1-methyl-2,3,4,5-tetrahydro-1H-3-benzazepine hydrochloride hemihydrate.

3. A method of inducing satiety comprising administering to an individual in need of such administration a therapeutically effective amount of (R)-8-chloro-1-methyl-2,3,4,5-tetrahydro-1H-3-benzazepine hydrochloride hemihydrate.

4. A method of controlling weight gain comprising administering to an individual in need of such administration a therapeutically effective amount of (R)-8-chloro-1-methyl-2,3,4,5-tetrahydro-1H-3-benzazepine hydrochloride hemihydrate.

* * * * *